United States Patent
Ishibiki

(10) Patent No.: US 7,087,012 B2
(45) Date of Patent: Aug. 8, 2006

(54) ENDOSCOPE HOOD

(75) Inventor: Kouta Ishibiki, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/894,217

(22) Filed: Jul. 19, 2004

(65) Prior Publication Data
US 2004/0260149 A1    Dec. 23, 2004

(30) Foreign Application Priority Data
Feb. 28, 2002  (JP)  ............. 2002/054817

(51) Int. Cl.
*A61B 1/00*    (2006.01)
(52) U.S. Cl. ................. 600/127; 600/129
(58) Field of Classification Search ........ 600/121–127, 600/129
See application file for complete search history.

(56) References Cited

U.S. PATENT DOCUMENTS

| | | | |
|---|---|---|---|
| 5,897,487 A * | 4/1999 | Ouchi | 600/127 |
| 6,855,108 B1 * | 2/2005 | Ishibiki et al. | 600/127 |
| 6,916,284 B1 * | 7/2005 | Moriyama | 600/127 |
| 2004/0077926 A1 * | 4/2004 | Moriyama | 600/101 |
| 2004/0077928 A1 * | 4/2004 | Moriyama | 600/127 |
| 2004/0082832 A1 * | 4/2004 | Moriyama | 600/101 |
| 2005/0043584 A1 * | 2/2005 | Nozue | 600/127 |

FOREIGN PATENT DOCUMENTS

| | | |
|---|---|---|
| JP | 56-75912 | 6/1981 |
| JP | 59-93413 | 5/1984 |
| JP | 60-13101 | 1/1985 |
| JP | 11-313795 | 11/1999 |
| JP | 2001-224550 | 8/2001 |

* cited by examiner

*Primary Examiner*—John P. Leubecker
(74) *Attorney, Agent, or Firm*—Scully, Scott, Murphy & Presser, P.C.

(57) ABSTRACT

At least one concave portion 40 is provided as a part of a protrusion 38 of an end portion of a hood body 37a while protruding frontward from the location of a front-end lens surface 34 with a protrusion length shorter than those of the parts other than the concave portion, an inclined surface 44 divergent frontward from the location of the front-end lens surface 34 is provided on the inside surface of at least one of the concave portions 40, and the angle β between the inside inclined surface 44b of the concave portion 40 and the front-end lens surface 34 is larger than the angle α between the inside surfaces of the other parts adjacent to the concave portion 40 and the front-end lens surface 34.

20 Claims, 9 Drawing Sheets

FIG. 5B FIG. 5A
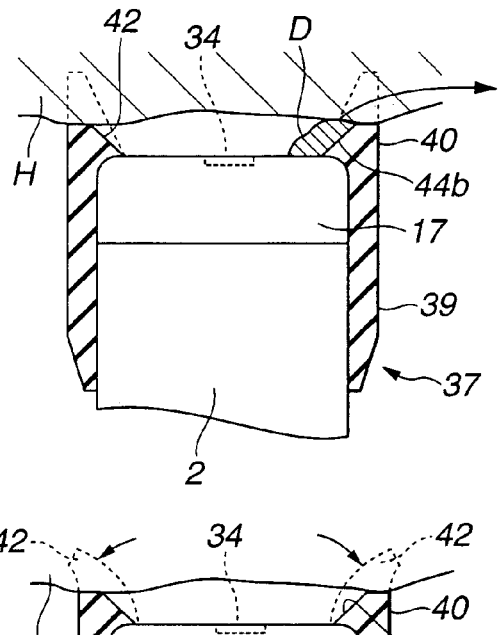
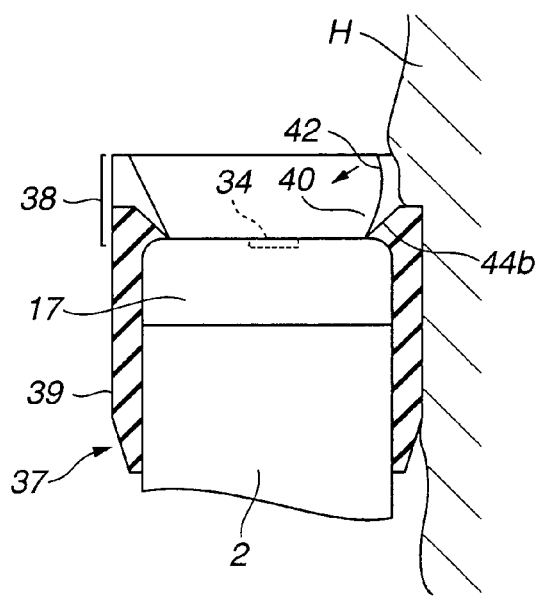
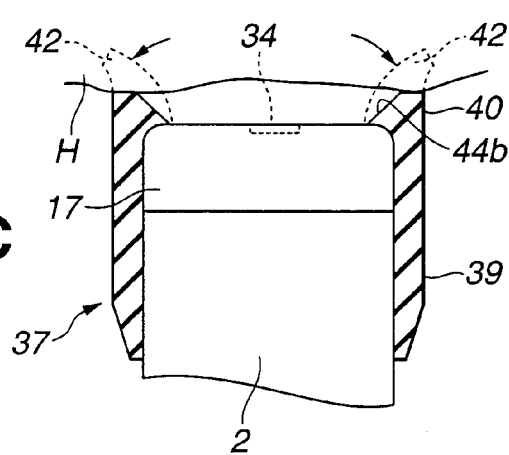
FIG. 5C
FIG. 6
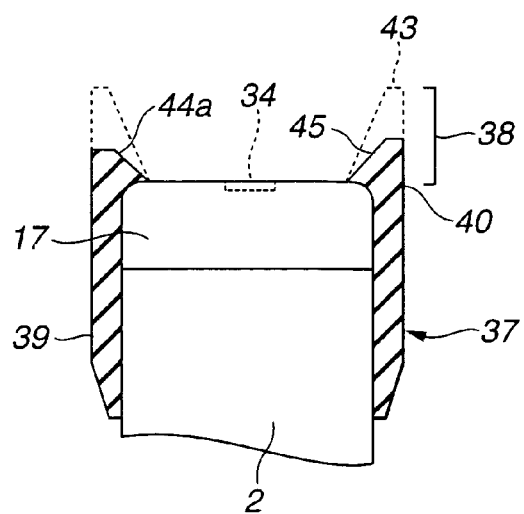

ENDOSCOPE HOOD

This application claims benefit of Japanese Application No. 2002-054817 filed on Feb. 28, 2002, and PCT Application No. PCT/JP03/02026 filed in Japan on Feb. 25, 2003, the contents of which are incorporated by this reference.

TECHNICAL FIELD

The present invention relates to an endoscope hood disposed at the distal end of an insertion portion of an endoscope.

BACKGROUND ART

An endoscope provided with an endoscope hood at the distal end of a slim insertion portion may be used. This endoscope hood includes a substantially cylindrical hood body. This hood body includes a fixation portion to be fixed to the distal end of the insertion portion of the endoscope. Furthermore, a protrusion protruding in the direction of the observational field of view of the endoscope is disposed at the end portion of this fixation portion. In the endoscope provided with such a hood, this endoscope hood prevents direct contact of a front-end lens surface of an observational optical system exposed at an end surface of the insertion portion distal end with a lumen medial wall surface.

Japanese Unexamined Utility Model Application Publication No. 56-75912 and Japanese Unexamined Patent Application Publication No. 59-93413 disclose configurations in which exhaust holes are provided on side wall portions of endoscope hoods in order to discharge filth and the like adhering to end surfaces of endoscopes.

The above-described Japanese Unexamined Utility Model Application Publication No. 56-75912 discloses an endoscope hood having a notch for serving an exhaust hole prepared by notching the hood up to the end surface of an insertion portion of the endoscope and a configuration in which a cylindrical hood body is notched in a slanting direction and the lowest part of the notch is flush with the end surface of an endoscope. The above-described Japanese Unexamined Patent Application Publication No. 59-93413 discloses a configuration in which a cylindrical hood body is notched in a slanting direction and the lowest part of the notch does not reach the end surface of an endoscope.

DISCLOSURE OF INVENTION

An endoscope hood which is integrally or detachably provided at the distal end of an insertion portion of an endoscope to be inserted into a lumen and which comprises a hood body for preventing direct contact of a front-end lens surface of an observational optical system exposed at an end surface of this distal end with a medial wall surface of the lumen and a protrusion protruding in the direction of the observational field of view of the endoscope while the protrusion is-disposed at the end portion of the hood body, wherein at least one concave portion is provided as a part of the protrusion while protruding frontward from the location of the front-end lens surface with a protrusion length shorter than those of the parts other than the concave portion and an inclined surface divergent frontward from the location of the front-end lens surface is provided on the inside surface of at least one of the concave portions, and wherein the angle between the inside inclined surface of the concave portion and the front-end lens surface is larger than the angle between the inside surfaces of the other parts adjacent to the concave portion and the front-end lens surface.

Another endoscope hood of the present invention includes a hood body for preventing direct contact of a front-end lens surface of an observational optical system exposed at an end surface of this distal end with the above-described lumen medial wall surface while the hood body is disposed at the distal end of an endoscope insertion portion to be inserted into a lumen and includes a protrusion protruding in the direction of the observational field of view of the above-described endoscope while the protrusion is disposed at the end portion of the above-described hood body, wherein an inclined surface divergent frontward from the location of the above-described front-end lens surface is provided on the inside perimeter surface of the above-described protrusion, wherein an concave portion is provided as a part of the above-described protrusion while protruding frontward from the location of the above-described front-end lens surface with a protrusion length shorter than those of the parts other than the concave portion, and wherein the angle between a second inside inclined surface of the above-described concave portion and the above-described front-end lens surface is larger than the angle between first inside inclined surfaces of the other parts adjacent to the above-described concave portion and the above-described front-end lens surface.

In addition, the endoscope hood of the present invention includes;

a hood body which has a first protrusion protruding frontward in the direction of the observation filed of view of the endoscope from the distal end of the insertion portion of the endoscope and a second protrusion formed adjacently to the first protrusion as a concave portion while protruding frontward in the direction of the observation field of view of the endoscope with a protrusion length shorter than that of the first protrusion, a first inclined surface which is provided on the inner surface of the first protrusion, the first inclined surface being divergent frontward from the location of the front-end lens surface of the endoscope, and a second inclined surface which is provided on the inner surface of the second protrusion, the second inclined surface being divergent frontward from the location of the front-end lens surface of the endoscope, wherein the angle defined by the second inclined surface of the second protrusion and the front-end lens surface is larger than the angle defined by the first inclined surface of the first protrusion and the front-end lens surface.

BRIEF DESCRIPTION OF THE DRAWINGS

FIG. 5A is a vertical sectional view of the key portion showing the condition in which the distal side of the endoscope hood in the first embodiment is in contact with a body cavity mucosa. FIG. 5B is a vertical sectional view of the key portion showing the condition in which the end-side outside perimeter surface of the protrusion in a modified example of the endoscope hood in the first embodiment is elastically deformed by the contact with a body cavity mucosa. FIG. 5C is a vertical sectional view of the key portion showing the condition in which a long convex portion of the end portion of the protrusion in a modified example of the first embodiment is elastically deformed by the contact with a body cavity mucosa.

FIG. 6 is a vertical sectional view of the key portion of an endoscope hood in a second embodiment of the present invention.

BEST MODE FOR CARRYING OUT THE INVENTION

The first embodiment of the present invention will be described below with reference to FIG. 1 to FIGS. 5A to 5C.

Figure 1:
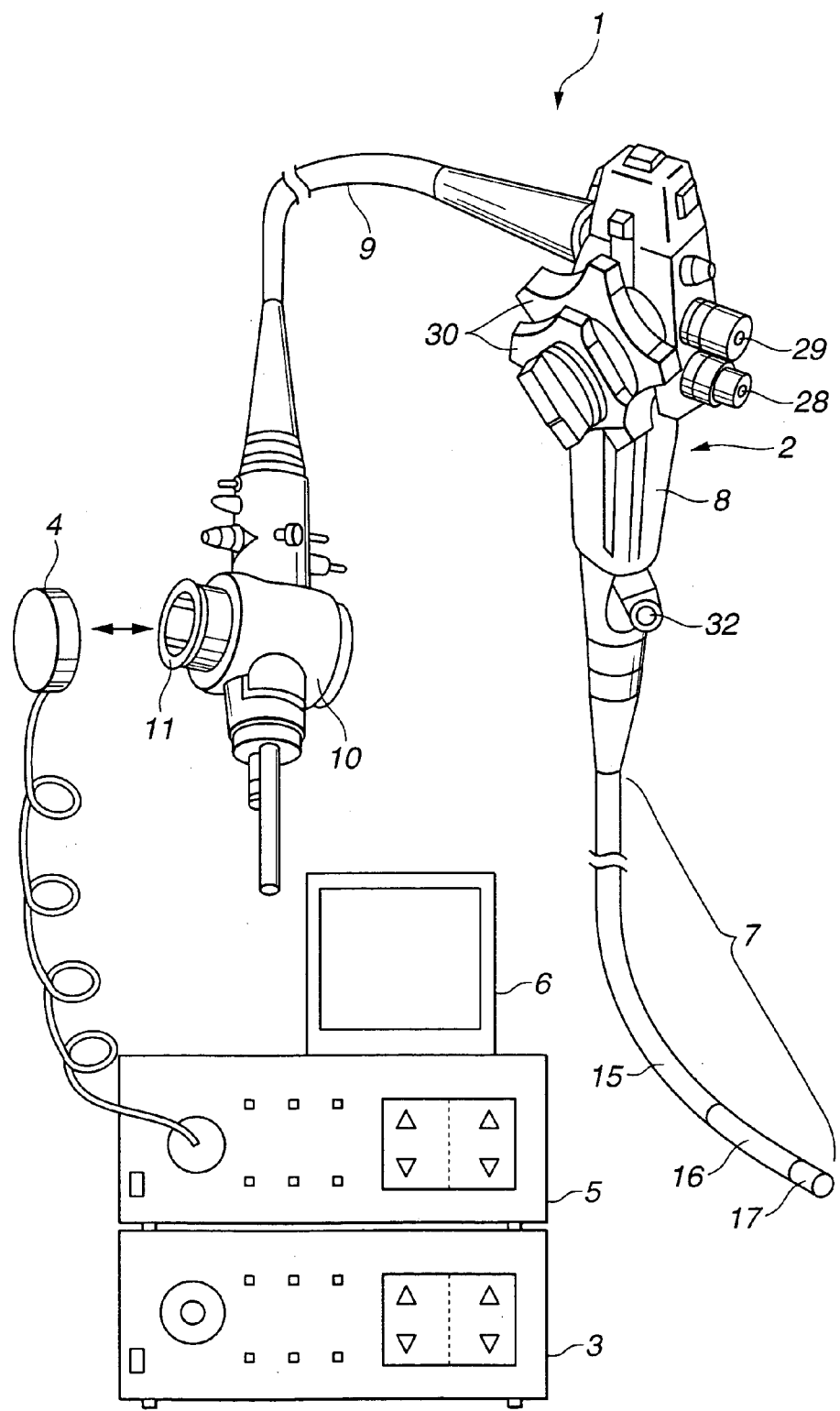
FIG. 1 is a perspective view showing the schematic configuration of a total endoscope apparatus in a first embodiment of the present invention.

FIG. 1 is a diagram showing the schematic configuration of a total endoscope apparatus 1 in the present embodiment. The endoscope apparatus 1 is primarily composed of an endoscope 2 provided with an image pickup device, a light source device 3 detachably connected to the endoscope 2, a video processor 5 connected to the endoscope 2 via a signal cable 4, and a monitor 6 for displaying an image. In this endoscope apparatus 1, illumination light emitted from the light source device 3 is supplied to a light guide provided in the endoscope 2. The video processor 5 controls an image pickup device of the endoscope 2 and, in addition, processes signals obtained from the image pickup device of the endoscope 2. An image corresponding to a subject image output from this video processor 5 is displayed on the monitor 6.

The endoscope 2 is provided with a slender insertion portion 7 having pliability. An operating portion 8 on hand is connected to the base end side of the insertion portion 7. The operating portion 8 is provided with an air and water supply operation button 28, a suction operation button 29, an angling-operation knob 30, and a treatment appliance insertion port 32.

A base end portion of a pliable connecting code 9 is connected to the side portion of the operating portion 8. A connector portion 10 is provided at the end portion of the connecting code 9 and is detachably connected to the light source device 3. An electric connector portion 11 is provided at the side portion of the connector portion 10. The signal cable 4 connected to the video processor 5 can be detachably connected to the electric connector portion 11.

The insertion portion 7 is provided with a slender flexible pliable tube 15 having pliability. A bending portion 16 capable of being curved is provided at the end side of the pliable tube 15. With respect to the above-described endoscope 2, bending operation of the bending portion 16 can be performed by operating the angling-operation knob 30 of the operating portion 8.

Figure 2A:
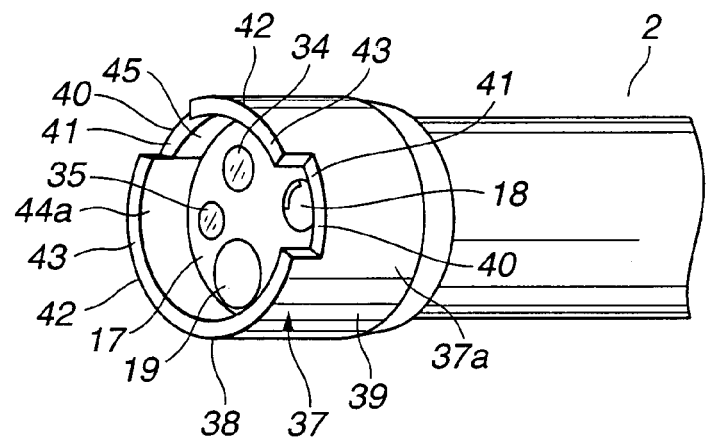
FIG. 2A is a perspective view showing a fitting portion of the endoscope hood in the first embodiment.
Figure 2B:
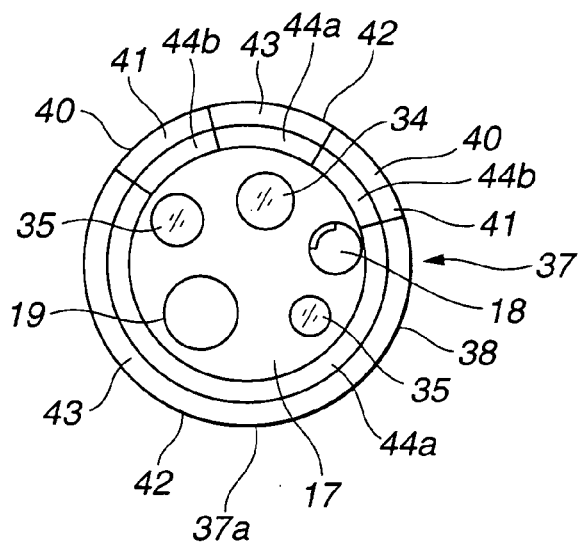
FIG. 2B is a front view showing the fitting portion of the endoscope hood in the first embodiment.

A distal end 17 is disposed at the front end of the insertion portion 7, and the distal end 17 is provided with an observational optical system, an illuminational optical system, and the like described below. As shown in FIG. 2A and FIG. 2B, each of an air and water supply nozzle 18, a suction port 19, a front-end lens surface 34 of the observational optical system, and two front-end lens surfaces 35 of the illuminational optical system is provided on the end surface of the distal end 17. A cleaning liquid or an air is ejected from the air and water supply nozzle 18 toward the front-end lens surface 34 which is an outside surface of the observational optical system by an air supply operation or a water supply operation of the air and water supply operation button 28 of the operating portion 8.

The suction port 19 is an opening in the end side of a treatment appliance channel, although not shown in the drawing, disposed in the insertion portion 7. The base end portion of the treatment appliance channel is connected to the treatment appliance insertion port 32 of the operating portion 8. A treatment appliance inserted from the treatment appliance insertion port 32 passes through the treatment appliance channel, and extends to the outside from the suction port 19. A suction operation through the suction port 19 is performed by operating the suction operation button 29 of the operating portion 8 in order to suction a liquid from a body cavity.

An endoscope hood 37 is detachably fitted to the distal end 17. According to the endoscope hood 37, direct contact of the front-end lens surface 34 of the observational optical system exposed at the end surface of the distal end 17 of the endoscope 2 with a medial wall surface of a lumen into which the endoscope 2 is inserted is prevented and, thereby, reduction in the field of view of the endoscope 2 is prevented.

The endoscope hood 37 is formed from a soft component, for example, vulcanized rubber, e.g., silicon rubber and fluororubber; and thermoplastic elastomers, e.g., urethane-based elastomers, acrylic-based elastomers, and olefin-based elastomers, or a hard resin, e.g., polysulfone. In the present embodiment, the endoscope hood 37 is formed from a soft component.

Figure 3A:
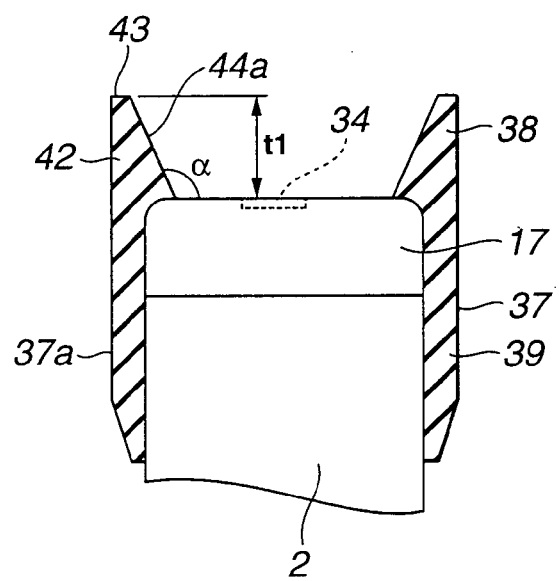
FIG. 3A is a vertical sectional view of the key portion showing a first inside inclined surface of a convex portion adjacent to a concave portion of the endoscope hood in the first embodiment.
Figure 3B:
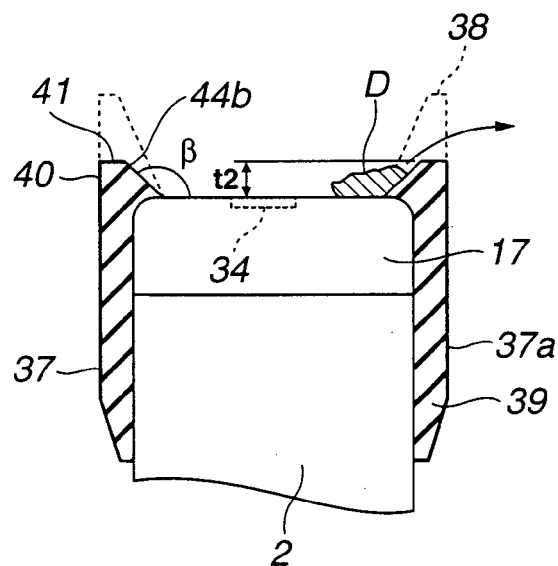
FIG. 3B is a vertical sectional view of the key portion showing a second inside inclined surface of a concave portion of the endoscope hood.

As shown in FIGS. 3A and 3B, this endoscope hood 37 includes a substantially cylindrical hood body 37a. The hood body 37a includes an endoscope fixation portion 39 having an inside diameter slightly smaller than or substantial equal to the outside diameter of the distal end 17 of the endoscope 2. The distal end 17 is press-fitted into the hood body 37a by elastic deformation of the endoscope fixation portion 39 and, thereby, the endoscope hood 37 is detachably fixed to the distal end 17.

Furthermore, the endoscope hood 37 includes a protrusion 38 protruding from the distal end 17 in the forward direction of the field of view of the observational optical system.

Two concave portions 40 are provided as parts of the end portion of the protrusion 38 in the circumferential direction, and each concave portion 40 has a protrusion length from the front-end lens surface 34 of the observational optical system shorter than those of the parts other than the concave portion 40. As shown in FIG. 3A, the length t1 of protrusion of an end surface 43 of each convex portion 42 adjacent to each concave portion 40 is adjusted at, for example, 4 mm from the location of the-front-end lens surface 34 of the observational optical system on the distal end 17. As shown in FIG. 3B, the length t2 of protrusion of an inside bottom 41 of each concave portion 40 is adjusted at, for example, 2 mm.

As shown in FIG. 3A, a tapered surface-shaped inclined surface 44a divergent frontward from the location of the front-end lens surface 34 of the observational optical system is provided on the inside perimeter surface of the convex portion 42. This first inclined surface 44a forms an angle α of about 130° with the surface of the front-end lens surface 34 of the observational optical system and the end surface of the distal end 17. As shown in FIG. 3B, a second inside inclined surface 44b of each concave portion 40 forms an angle β of about 160° with the surface of the front-end lens surface 34 of the observational optical system and the end surface of the distal end 17. In this manner, the angle β between the second inside inclined surface 44b of each concave portion 40 and the front-end lens surface 34 is adjusted to be larger than the angle α between the first inside inclined surface 44a of each convex portion 42 adjacent to each concave portion 40 and the front-end lens surface 34 (β>α).

The operation of the above-described configuration will be described below.

In the present embodiment, as shown in FIG. 3B, filth D, e.g., mucus and filth, may enter the inside of the protrusion 38 during an inspection, wherein the insertion portion 7 of the endoscope 2 is inserted into a body cavity and the interior of the body is inspected with the endoscope. At this time, since the angle β of the second inclined surface 44b is larger than α in the endoscope hood 37 of the present embodiment, two concave portions 40 at the end portion of the protrusion 38 serves as flow paths for discharge. Consequently, as indicated by an arrow shown in FIG. 3B, filth D, e.g., mucus and filth, inside the protrusion 38 is led along the second inclined surface 44b toward the outside, and is discharged from the inside bottom 41 of the concave portion 40 to the outside. As a result, even when the filth D, e.g., mucus and filth, enters the inside of the protrusion 38 of the endoscope hood 37, these do not accumulate inside the protrusion 38, and are drawn along the second inclined surface 44b to the outside, so that the discharge can be smoothly performed.

Figure 4A:
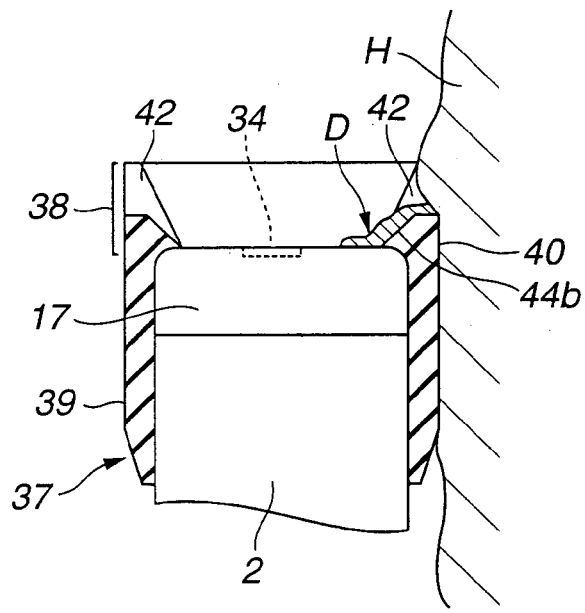
FIG. 4A shows the operation of the endoscope hood in the first embodiment, and is a vertical sectional view of the key portion in the condition in which the concave portion of the protrusion is in contact with a body cavity mucosa during inspection.
Figure 4B:
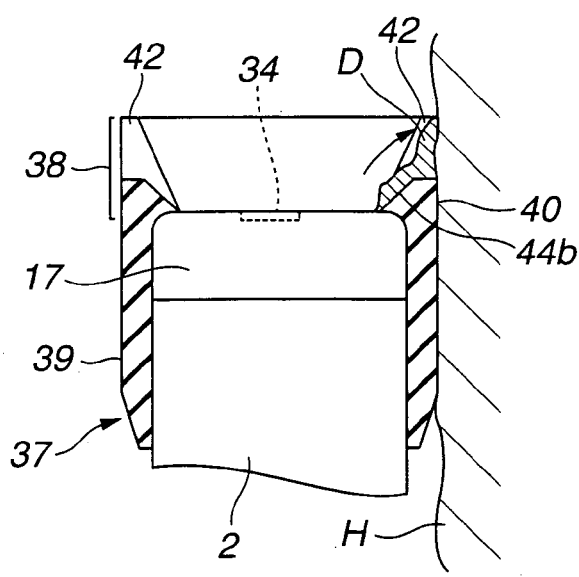
FIG. 4B is a vertical sectional view of the key portion in the condition in which filth and the like are drawn along the second inside inclined surface of the concave portion of the endoscope hood to the outside, and are discharged.

Furthermore, even when filth D, e.g., mucus and filth, which has a high viscosity and resists flowing to the outside is adhered to the surface of the second inclined surface 44b, as shown in FIG. 4A, the filth D is drawn along the second inside inclined surface of the concave portion 40 of the endoscope hood 37 to the outside by the contact between the concave portion 40 of the protrusion 38 of the endoscope hood 37 in the present embodiment with a body cavity mucosa H during the inspection, and the filth D is discharged as shown in FIG. 4B.

The above-described configuration exerts the following effects. In the endoscope hood 37 of the present embodiment, two concave portions 40 are provided as parts of the end portion of the protrusion 38 in the circumferential direction while each concave portion 40 has a protrusion length from the front-end lens surface 34 of the observational optical system shorter than those of the parts other than the concave portion 40, the angle β between the second inside-inclined surface 44b of each of the two concave portions 40 of the protrusion 38 of the end portion of the hood body 37a and the front-end lens surface 34 of the observational optical system is adjusted to be larger than the angle α between the first inside inclined surface 44a of each convex portion 42 adjacent to each concave portion 40 and the front-end lens surface 34 of the observational optical system and, therefore, the concave portion 40 is open toward the outside. In this manner, even when filth D, e.g., mucus and filth, enters the inside of the protrusion 38, these do not accumulate inside the protrusion 38, and are drawn along the second inside inclined surface 44b of the concave portion 40 to the outside, so that the discharge can be smoothly performed.

Furthermore, as shown in FIG. 5A, the end side is allowed to contact the body cavity mucosa H, and the body cavity mucosa H is allowed to contact the filth D, e.g., mucus and filth, on the second inclined surface 44b, so that the filth D, e.g., mucus and filth, can be discharged to the outside from the second inclined surface 44b.

When the protrusion 38 is formed from a soft component, as shown in FIGS. 5B and 5C, the convex portion 42 having a large protrusion length is allowed to elastically deform by contact with the body cavity mucosa H. In this manner, as shown in FIGS. 5B and 5C, when the end side of the endoscope hood 37 is allowed to contact the body cavity mucosa H, the filth D, e.g., mucus and filth, located on the second inclined surface 44b of each concave portion 40 and the inside bottom 41 of each concave portion 40 is easily allowed to contact with the body cavity mucosa H and, thereby, the filth D can be discharged from the second inclined surface 44b to the outside by the contact between the body cavity mucosa H and the filth D, e.g., mucus and filth. Consequently, there is an effect that the filth D, e.g., mucus and filth, resists accumulating inside the concave portion 40.

Since the inside bottom 41 of each concave portion 40 is disposed in the location protruding frontward from the front-end lens surface 34 of the observational optical system and the end surface of the distal end 17 as well, there are effects that the function of the endoscope hood 37 is not reduced, and the protrusion 38 resists being damaged. Consequently, the endoscope hood 37 having excellent observation performance can be provided, wherein an excellent function as the hood is exhibited, the protrusion 38 resists being damaged, and filth D, e.g., mucus and filth, resists accumulating inside the hood body 37a.

In the present embodiment, the inside perimeter surface of the convex portion 42 of the protrusion 38 is the inclined surface 44a, the inside perimeter surface of the concave portion 40 is the inclined surface 44b, and both of them are inclined surfaces divergent frontward. However, the inside perimeter surface of the convex portion 42 may not be an inclined surface, and be formed substantially perpendicular to the surface of the front-end lens surface 34 and the end surface of the distal end 17. At least the inclined surface 44b must be formed into the above-described inclined surface. In the present embodiment, since the inclined surface 44a is provided on the inside perimeter surface of the convex portion 42, the height difference between the inside perimeter surface of the convex portion 42 (in the present embodiment, the inclined surface 44a) and the inclined surface 44b of the concave portion 40 is reduced and, therefore, mucus and filth can be smoothly transferred to the inclined surface 44b compared with the case where the inside perimeter surface of the convex portion 42 is perpendicular. Since the angle between the root of the convex portion 42 and the end surface of the distal end 17 is an obtuse angle, the mucus and filth resist accumulating in the corner between the root of the convex portion 42 and the end surface of the distal end 17, and are smoothly transferred to the inclined surface 44b. Since the thickness of the root side of the convex portion 42 is increased, reduction in the strength of the protrusion 38 due to provision of the convex portion 40 can be prevented.

FIG. 6 shows the second embodiment of the present invention. In the present embodiment, the end surface of the inside bottom 41 of each concave portion 40 of the protrusion 38 of the endoscope hood 37 in the first embodiment (refer to FIG. 1 to FIGS. 5A to 5C) is formed into a continuous surface 45 inclined substantially at the same angle as that of the second inclined surface 44b.

Consequently, in the present embodiment, even when filth D, e.g., mucus and filth, enters the inside of the protrusion 38, the filth D is transferred along the second inclined surface 44b to the end surface of the inside bottom 41 of each concave portion 40 of the protrusion 38 and, thereafter, the filth D can be smoothly transferred to the outside of the protrusion 38 via the continuous surface 45 inclined substantially at the same angle as that of the second inclined surface 44b. Since the filth D, e.g., mucus and filth, can be further smoothly transferred to the outside of the protrusion 38 compared with that in the endoscope hood 37 of the first embodiment, there is an effect that discharge can be further easily performed.

Figure 7A:
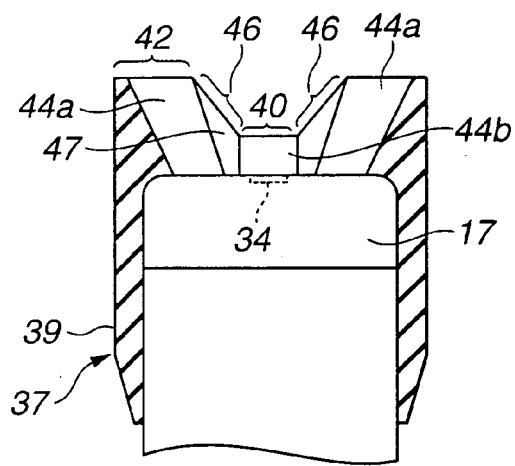
FIG. 7A is a vertical sectional view of the key portion of an endoscope hood in a third embodiment of the present invention.
Figure 7B:
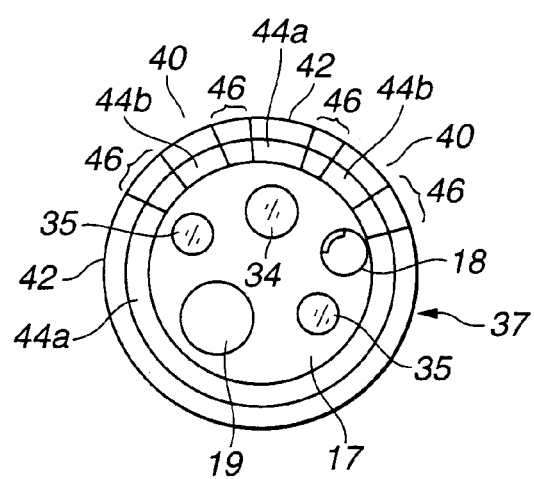
FIG. 7B is a front view showing the fitting portion of the hood in the endoscope.
Figure 7C:
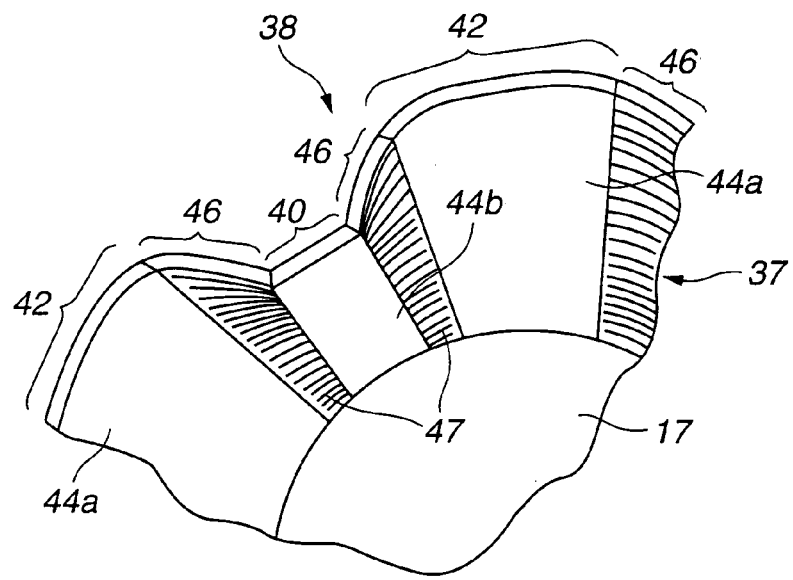
FIG. 7C is a perspective view of the key portion showing a concave portion of the endoscope hood.

FIGS. 7A to 7C show the third embodiment of the present invention. In the present embodiment, the configuration of the endoscope hood 37 in the first embodiment (refer to FIG. 1 to FIGS. 5A to 5C) is changed as described below. Since the basic configuration of the endoscope hood 37 in the present embodiment is substantially the same as that in the first embodiment, the same elements as those in the first embodiment are indicated by the same reference numerals, explanations thereof are not repeated hereafter, and different elements will be described.

The protrusion 38 of the endoscope hood 37 in the present embodiment includes a transition portion 46 between each concave portion 40 and each convex portion 42, and the transition portion 46 is formed by gradually changing the protrusion length of the protrusion 38. The second inside inclined surface 44b of the concave portion 40 and the first inside inclined surface 44a of the convex portion 42 are formed similar to those in the first embodiment.

Furthermore, a connection surface portion 47 for connecting the second inclined surface 44b and the first inclined surface 44a without causing a significant height difference therebetween is provided on the inside surface side of the transition portion 46. This connection surface portion 47 may be a flat surface, be a curved surface in a gently concave shape, or be a curved surface in a gently convex shape, as long as significant unevenness does not occur.

With respect to the endoscope hood 37 in the present embodiment having the above-described configuration, since the transition portion 46 is provided between each concave portion 40 and each convex portion 42 in the protrusion 38, and the transition portion 46 is formed by gradually changing the protrusion length of the protrusion 38, the height difference between each concave portion 40 and each convex portion 42 in the protrusion 38 can be reduced. Since there is no height difference which causes unevenness between the inside surface 44 of the protrusion 38 and each concave portion 40, the filth D, e.g., mucus and filth, present in the inside of the protrusion 38 does not stay, and can smoothly transfer to the concave portion 40, so that the filth D present in the inside of the protrusion 38 is further easily discharged.

Since the transition portion 46 is provided and the connection surface portion 47 for connecting the second inclined surface 44b and the first inclined surface 44a without causing a significant height difference is provided on the inside surface side, the area of the port of the protrusion 38 for discharging the filth D, e.g., mucus and filth, to the outside can be increased. Consequently, the filth D present in the inside of the protrusion 38 is further easily discharged.

In the present embodiment, parts of the protrusion 38 which have small protrusion lengths are reduced compared with the case where the aperture area of the concave portion 40 of the protrusion 38 having small protrusion length is simply increased and, therefore, the function as a hood is not impaired. Since parts occupied by the convex portions 42 of the protrusion 38 having a large protrusion length is not reduced, the convex portion 42 does not become susceptible to damage. Consequently, there is an effect of providing the endoscope hood 37, wherein the function as a hood is not impaired, and mucus and filth further resist accumulating.

Figure 8:
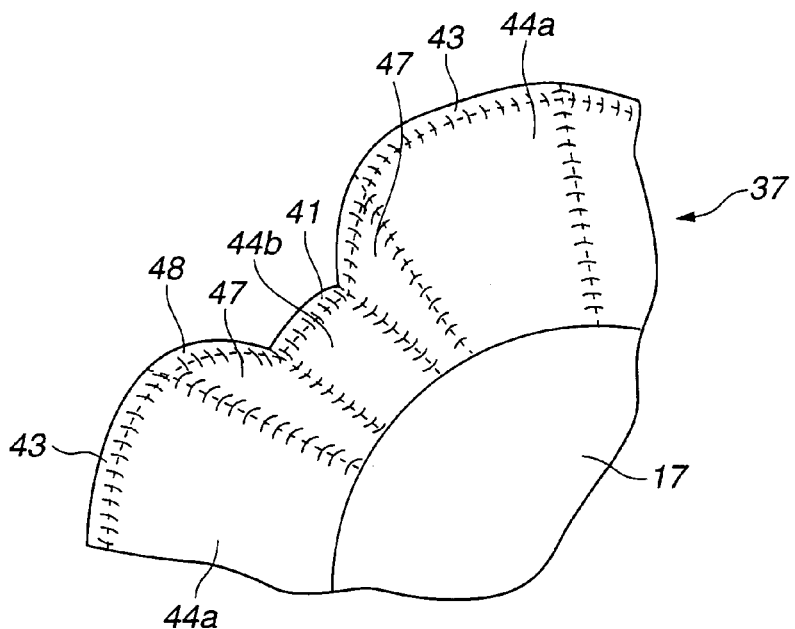
FIG. 8 is a perspective view of the key portion in a modified example of the endoscope hood in the third embodiment.

FIG. 8 shows a modified example of the endoscope hood in the third embodiment (refer to FIGS. 7A to 7B). In the present modified example, the connection portion between the connection surface portion 47 and the second inclined surface 44b, the connection portion between the connection surface portion 47 and the first inclined surface 44a, the connection portion between the first inclined surface 44a and the end surface 43 of the convex portion 42, the connection portion between the second inclined surface 44b and the end surface of the inside bottom 41 of each concave portion 40, and the connection portion between the connection surface portion 47 and the end portion 48 thereof are chamfered into the shape of a curved surface (a rounded shape) for smooth connection, with respect to the protrusion 38 of the endoscope hood 37 in the third embodiment.

FIG. 9 to FIG. 14 show the fourth embodiment of the present invention. In the present embodiment, the configuration of the endoscope hood 37 in the first embodiment (refer to FIG. 1 to FIGS. 5A to 5C) is changed as described below. Since the basic configuration of the endoscope hood 37 in the present embodiment is substantially the same as that in the first embodiment, the same elements as those in the first embodiment are indicated by the same reference numerals, explanations thereof are not repeated hereafter, and different elements will be described.

Figure 13:
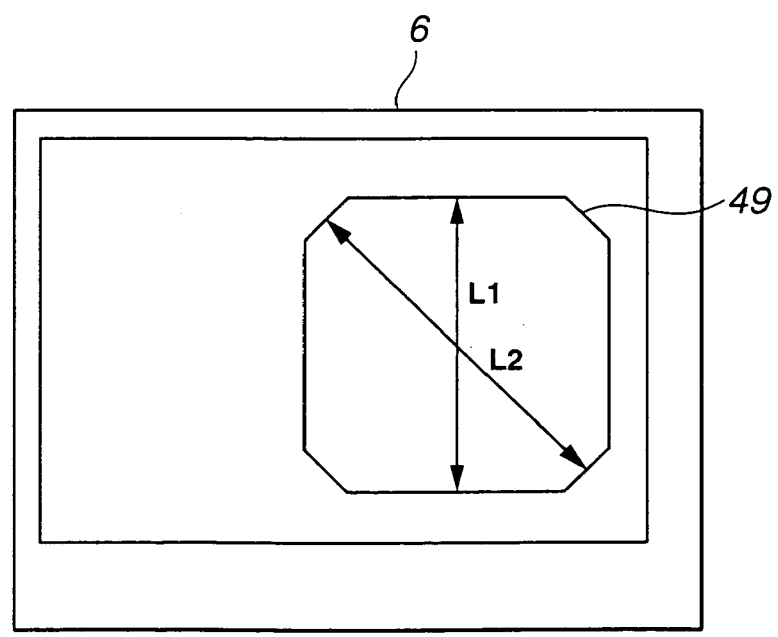
FIG. 13 is a front view showing an observation image of an observational optical system of an endoscope, displayed on a monitor of an endoscope apparatus.
Figure 14:
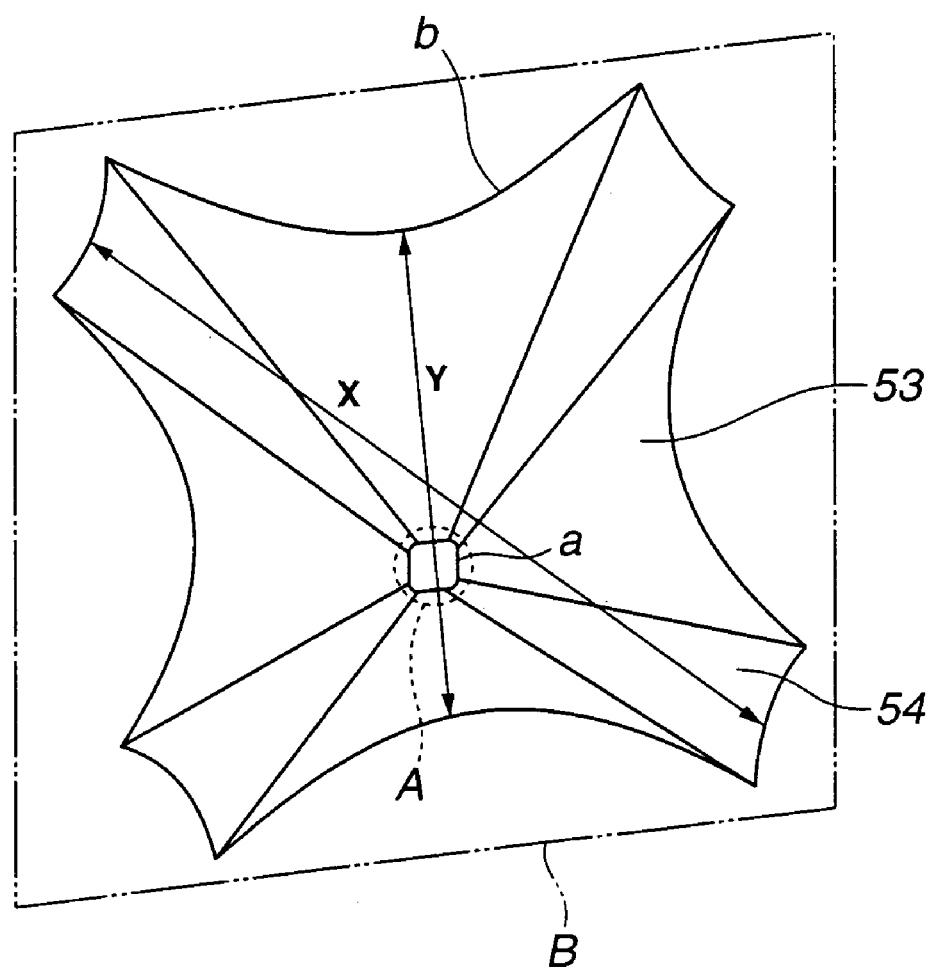
FIG. 14 is a diagram for explaining a region of observational field of view of an observational optical system of an endoscope when the observation image shown in FIG. 13 is displayed.

The endoscope hood 37 in the present embodiment is formed in order that an observation image 49 of the observational optical system of the endoscope 2 is displayed on a monitor 6 while being shaped into a substantially tetragonal shape, as shown in FIG. 13. FIG. 14 shows a region 53 of observational field of view of the observational optical system of the endoscope 2 when such an observation image 49 is displayed. In FIG. 14, A indicates the front-end lens surface 34 of the observational optical system of the endoscope 2, and B indicates an end-side virtual plane at an arbitrary distance (length) from this lens surface 34.

The range of observational field of view of the observational optical system of the endoscope 2 on the surface A is a region a, and the range of the observational field of view of the observational optical system of the endoscope 2 on the plane B is a region b. The space between the region a and the region b is the region 53 of observational field of view of the observational optical system of the endoscope 2.

The side surface in the region 53 of observational field of view of the observational optical system of the endoscope 2 is a curved surface 54 formed by gathering of lights from different angles. With respect to the observation image 49 of the observational optical system of the endoscope 2, as shown in FIG. 13, the length L2 in a diagonal direction Y is longer than the length L1 in a opposite side direction and, therefore, with respect to the region 53 of observational field of view of the observational optical system of the endoscope 2, the angle of view in the diagonal direction X is larger, as shown in FIG. 14.

The observational optical system commonly used for the endoscope 2 has a characteristic that the degree of image compression is increased as the location becomes farther from the center of an optical axis due to aberration of the optical system. Consequently, the shape of the region b of the range of observational field of view of the observational optical system of the endoscope 2 on the plane B is not the same shape as that of the observation image 49 of the observational optical system of the endoscope 2, the region in the diagonal direction X is increased, and the angle of view-becomes larger than those in the other directions.

Figure 9:
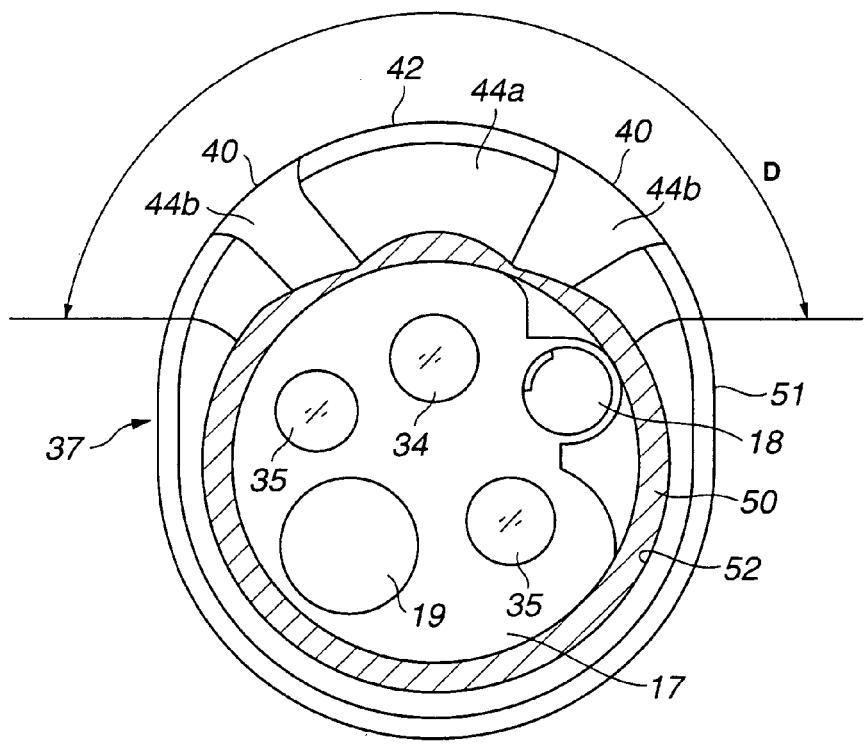
FIG. 9 is a front view showing the schematic configuration of an endoscope hood in a fourth embodiment of the present invention.

When the protrusion 38 of the endoscope hood 37 has a constant protrusion length, at least a part of the protrusion 38 overlaps the region 53 of observational field of view of the observational optical system of the endoscope 2. Therefore, in the present embodiment, at least a part of the protrusion 38 of the endoscope hood 37 is formed into substantially the same shape as the curved surface 54 of the side surface in the region 53 of observational field of view of the observational optical system of the endoscope 2 or into the shape not overlapping the curved surface 54 in order to avoid overlapping with the region 53 of observational field of view of the observational optical system of the endoscope 2. Here, as shown in FIG. 9, the part indicated by range D in the protrusion 38 of the endoscope hood 37 has the shape reflecting the curved surface 54 of the side surface in the region 53 of observational field of view of the observational optical system of the endoscope 2.

The first inside inclined surface 44a of the convex portion 42 of the endoscope hood 37 is in the shape of a curved surface resulting from a slight shift of the curved surface 54 of the side surface in the region 53 of observational field of view of the observational optical system of the endoscope 2 in the direction suitable for avoiding overlapping with the curved surface 54. The concave portion 40 for discharging the above-described filth D, e.g., mucus and filth, is disposed at the part where the protrusion 38 has a minimum protrusion length in order to ensure a maximum angle of view and to avoid overlapping with the region 53 of observational field of view. The second inclined surface 44b of the concave portion 40 has the protrusion length that can avoid overlapping with the curved surface 54. A tapered surface 50 is continuously provided all around the inside perimeter side of the second inside inclined surfaces 44b of the concave portions 40 and the first inside inclined surface 44a of the convex portion 42 at the diagonally shaded position shown in FIG. 9.

Figure 10:
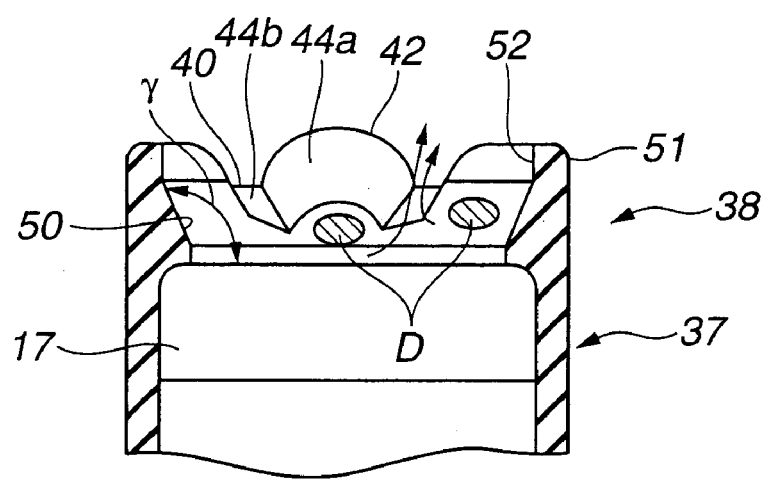
FIG. 10 is a vertical sectional view of the key portion showing a fitting condition of an endoscope hood in a fourth embodiment.
Figure 11:
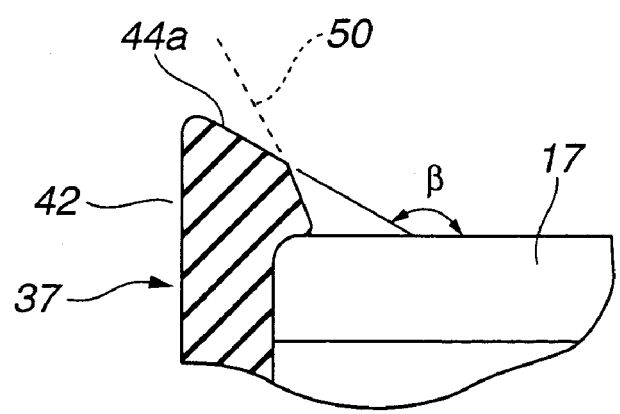
FIG. 11 is a vertical sectional view of the key portion showing an angle β between a first inside inclined surface of a convex portion of an endoscope hood and a front-end lens surface of an observational optical system of the endoscope in the fourth embodiment.
Figure 12:
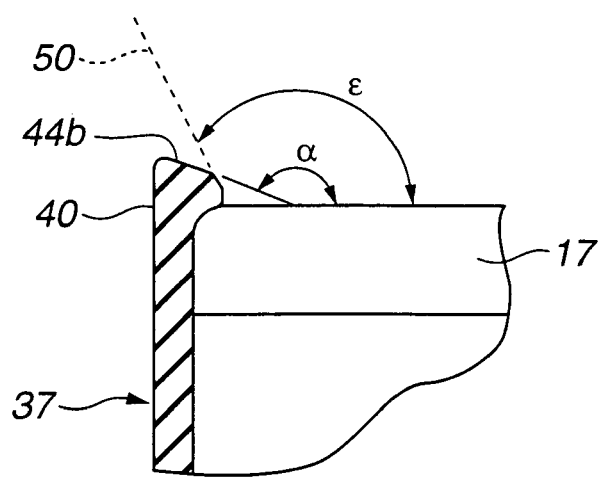
FIG. 12 is a vertical sectional view of the key portion showing an angle α between a second inside inclined surface of a concave portion of the endoscope hood and the front-end lens surface of the observational optical system of the endoscope in the fourth embodiment.

The second inside inclined surfaces 44b of the concave portions 40 are adjusted to satisfy the following relationship with respect to the first inside inclined surface 44a of the convex portion 42 and the inside surface 52 of the other convex portion 51 at every position on these curved surfaces. The angle between the inside surface 52 of the convex portion 51 and the front-end lens surface 34 of the observational optical system of the distal end 17 is represented by $\gamma$, as shown in FIG. 10, the angle between the first inside inclined surface 44a of the convex portion 42 and the front-end lens surface 34 of the observational optical system of the distal end 17 is represented by $\beta$, as shown in FIG. 11, and the angle between the second inside inclined surface 44b of each concave portion 40 and the front-end lens surface 34 is represented by $\alpha$, as shown in FIG. 12. Each of them is adjusted to satisfy $\alpha>\beta$ and $\alpha>\gamma$.

Furthermore, as shown in FIG. 12, the angle between the tapered surface 50 in the inside perimeter side of the second inclined surfaces 44b and the front-end lens surface 34 of the observational optical system of the distal end 17 is represented by $\epsilon$, and $\alpha$ is adjusted to satisfy the relationship of $\alpha>\epsilon$ with respect to the angle $\epsilon$ of the tapered surface 50.

The above-described configuration exerts the following effects. In the endoscope hood 37 of the present embodiment having the above-described configuration, the continuous tapered surface 50 is provided all around the inside perimeter of the protrusion 38 while being in contact with each of the inside perimeter side of the second inside inclined surfaces 44b of the concave portions 40 and the first inside inclined surface 44a of the convex portion 42. Consequently, the filth D, e.g., mucus and filth, present in the inside of the endoscope hood 37 can be smoothly transferred to the second inclined surfaces 44b of the concave portions 40 via the tapered surface 50 and, therefore, the filth D, e.g., mucus and filth, present in the inside of the endoscope hood 37 can be further easily discharged. As a result, there is an effect of providing the endoscope hood 37, wherein the filth D, e.g., mucus and filth, further resists accumulating.

Since the concave portions 40 for discharging the filth D, e.g., mucus and filth, are disposed at the parts where the region 53 of observational field of view of the observational optical system of the endoscope 2 and the protrusion 38 of the endoscope hood 37 significantly overlap each other, parts of the protrusion 38 of the endoscope hood 37 which have small protrusion lengths can be minimized, and there is an effect that the function as a hood is not impaired. Consequently, there is an effect of providing the endoscope 2 having an excellent field of view, wherein the endoscope hood 37 can be prevented from entering the field of view without impairing the function of the endoscope hood 37.

The present invention is not limited to each of the above-described embodiments. For example, the endoscope hood 37 shown in each of the above-described embodiments is detachably fitted to the distal end of the insertion portion 7 of the endoscope 2. However, the endoscope hood 37 may be integrally provided at the distal end of the insertion portion 7 of the endoscope 2. The endoscope hood 37 may be formed from a hard component instead of the soft component. Furthermore, the protrusion length of the protrusion 38 of the endoscope hood 37, the number of the concave portions, and the sizes are not limited to each of the above-described embodiments, and these can be adjusted at will. It is essential that at least one concave portion is provided and an inclined surface is provided on the inside perimeter surface of at least one of the concave portions.

In each of the above-described embodiments, the tapered surface-shaped inclined surface 44 on the inside perimeter surface of the protrusion 38 is connected to the end surface of the insertion portion 7 of the endoscope 2 while the front-end lens surface 34 of the observational optical system is disposed on the end surface. Therefore, there is an effect that the filth D, e.g., mucus and filth, adhering to the end surface of the insertion portion 7 of the endoscope 2 is easily discharged.

As a matter of course, any modification can be performed within the scope of the present invention.

INDUSTRIAL APPLICABILITY

As described above, according to the present invention, the inclined surface divergent frontward from the location of the front-end lens surface is provided on the inside perimeter surface of the protrusion in the distal end of the hood body, the concave portion is provided as a part of the protrusion while protruding frontward from the location of the front-end lens surface with a protrusion length shorter than those of the other parts, and the angle between the second inside inclined surface of the concave portion and the front-end lens surface is larger than the angle between first inside inclined surfaces of the other parts adjacent to the concave portion and the front-end lens surface. Consequently, the function of the hood body is not reduced, the hood body is allowed to resist being damaged, mucus and filth are allowed to resist accumulating inside the hood body, and the observation performance can be improved.

The invention claimed is:

1. An endoscope hood which is integrally or detachably provided at the distal end of an insertion portion of an endoscope to be inserted into a lumen and which comprises a hood body for preventing direct contact of a front-end lens surface of an observational optical system exposed at an end surface of this distal end with a medial wall surface of the lumen and a protrusion protruding in the direction of an observational field of view of the endoscope while the protrusion is disposed at an end portion of the hood body,
wherein at least one concave portion is provided as a part of the protrusion while protruding frontward from the location of the front-end lens surface with a protrusion length shorter than those of parts other than the concave portion and an inclined surface divergent frontward from the location of the front-end lens surface is provided on an inside surface of at least one of the concave portions, and
wherein the angle between the inside inclined surface of the concave portion and the front-end lens surface is larger than the angle between inside -surfaces of the other parts adjacent to the concave portion and the front-end lens surface.

2. The endoscope hood according to claim 1,
wherein the inclined surface of the concave portion is provided as a surface continuing from an end surface of the concave portion.

3. The endoscope hood according to claim 1,
wherein the inclined surface of the concave portion is connected to a surface on which the observational optical system is disposed at the distal end of the endoscope.

4. The endoscope hood according to claim 1,
wherein connection surfaces are provided between the inclined surface of the concave portion and the inside surfaces of the other parts adjacent to the concave portion in order to connect these surfaces.

5. The endoscope hood according to claim 1,
wherein a continuous connection surface is provided while being in contact with the inclined surface of the concave portion and the inside surfaces of the other parts adjacent to the concave portion.

6. The endoscope hood according to claim 1,
wherein the protrusion is made from an elastically deformable soft elastic component.

7. The endoscope hood according to claim 1,
wherein the concave portion is provided in the location where large interference occurs between a region of the observational field of view of the observational optical system and the protrusion.

8. An endoscope hood comprising a hood body for preventing direct contact of a front-end lens surface of an observational optical system exposed at an end surface of a distal end with a medial wall surface of the lumen while the hood body is disposed at the distal end of an insertion portion of an endoscope to be inserted into a lumen and comprising a protrusion protruding in the direction of an observational field of view of the endoscope while the protrusion is disposed at an end portion of the hood body,
wherein an inclined surface divergent frontward from the location of the front-end lens surface is provided on an inside perimeter surface of the protrusion,
wherein a concave portion is provided as a part of the protrusion while protruding frontward from the location of the front-end lens surface with a protrusion length shorter than those of parts other than the concave portion, and
wherein the angle between an inside inclined surface of the concave portion and the front-end lens surface is larger than the angle between inside inclined surfaces of the other parts adjacent to the concave portion and the front-end lens surface.

9. The endoscope hood according to claim 8,
wherein the inclined surface of the concave portion is connected to a surface on which the observational optical system is disposed at the distal end of the endoscope.

10. The endoscope hood according to claim 8,
wherein connection surfaces are provided between the inclined surface of the concave portion and the inside surfaces of the other parts adjacent to the concave portion in order to connect these surfaces.

11. The endoscope hood according to claim 8,
wherein a continuous connection surface is provided while being in contact with the inclined surface of the concave portion and the inside surfaces of the other parts adjacent to the concave portion.

12. The endoscope hood according to claim 8,
wherein the protrusion is made from an elastically deformable soft elastic component.

13. The endoscope hood according to claim 8, wherein the concave portion is provided in the location where large interference occurs between a region of the observational field of view of the observational optical system and the protrusion.

14. An endoscope hood, comprising:

a hood body having a first protrusion protruding frontward in the direction of an observation field of view of an endoscope from a distal end of an insertion portion of the endoscope and a second protrusion formed adjacently to the first protrusion as a concave portion while protruding frontward in the direction of the observation field of view of the endoscope with a protrusion length shorter than that of the first protrusion;

a first inclined surface provided on an inner surface of the first protrusion, the first inclined surface being divergent frontward from the location of a front-end lens surface of the endoscope; and a second inclined surface provided on an inner surface of the second protrusion, the second inclined surface being divergent frontward from the location of the front-end lens surface of the endoscope, wherein the angle defined by the second inclined surface of the second protrusion and the front-end lens surface is larger than the angle defined by the first inclined surface of the first protrusion and the front-end lens surface.

15. The endoscope hood according to claim 14, wherein the second inclined surface of the second protrusion is provided as a surface continuing from an end surface of the second protrusion.

16. The endoscope hood according to claim 14, wherein the second inclined surface of the second protrusion is connected to a surface on which the observation optical system is disposed at the distal end of the endoscope.

17. The endoscope hood according to claim 14, wherein connecting surfaces are provided between the second inclined surface of the second protrusion and the first inclined surface of the first protrusion adjacent to the second protrusion in order to connect these surfaces.

18. The endoscope hood according to claim 14, wherein a continuous connection surface is provided while being in contact with the second inclined surface of the second protrusion and the first inclined surface of the first protrusion adjacent to the second protrusion.

19. The endoscope hood according to claim 14, wherein the first and second protrusions are made from an elastically deformable soft elastic component.

20. The endoscope hood according to claim 14, wherein the second protrusion is provided in the location where large interference occurs between a region of the observation field of view of the observation optical system and the first protrusion.

\* \* \* \* \*